US006367932B1

(12) United States Patent
Donaldson

(10) Patent No.: US 6,367,932 B1
(45) Date of Patent: Apr. 9, 2002

(54) APPARATUS AND METHOD FOR VISUAL FIELD TESTING

(75) Inventor: William Blair Macgregor Donaldson, Aberdeen (GB)

(73) Assignee: BID Instruments Limited, Aberdeen (GB)

( * ) Notice: Subject to any disclaimer, the term of this patent is extended or adjusted under 35 U.S.C. 154(b) by 0 days.

(21) Appl. No.: 09/530,328

(22) PCT Filed: Oct. 29, 1998

(86) PCT No.: PCT/GB98/03240

§ 371 Date: Jun. 27, 2000

§ 102(e) Date: Jun. 27, 2000

(87) PCT Pub. No.: WO99/22638

PCT Pub. Date: May 14, 1999

(30) Foreign Application Priority Data

Oct. 30, 1997 (GB) ................................. 9722949

(51) Int. Cl.$^7$ .................................................. A61B 3/02
(52) U.S. Cl. ....................................................... 351/237
(58) Field of Search ................................. 351/246, 237, 351/239, 243, 224, 238, 209, 210, 226, 222

(56) References Cited

U.S. PATENT DOCUMENTS 5,920,375 A * 7/1999 Fahle et al. .................. 351/246

* cited by examiner

Primary Examiner—George Manuel
(74) Attorney, Agent, or Firm—Woodcock Washburn LLP

(57) ABSTRACT

An apparatus for ocular is provided wit means (2, 3) for displaying targets (T1, T2) means (4) for tracking eye movement and means (5) for controlling the display of targets (T1, T2) on a screen. A method comprises arranging the control means (5) to choreograph display of the targets (T1, T2 . . .) at different positions at the screen (2) depending on whether the eye tracking means (4) detects that an observer is directly looking at the target.

10 Claims, 2 Drawing Sheets

APPARATUS AND METHOD FOR VISUAL FIELD TESTING

The present invention relates to an apparatus and method for the measurement of a visual field. In this respect, there are a number of existing tests for measuring and building up a visual field, such as for example the Bjerrum test, the Static Perimetry test and the Optokinetic test.

Briefly, in the Bjerrum test, a patient as the observer looks at a spot in the centre of a black screen throughout the test. A white or coloured test target at the end of black rod held by an examiner is moved from a non-seeing to a seeing area and a note is made of the position when the target is first claimed to be seen by the observer. By doing this in different areas, a visual field is built up.

With the Static Perimetry test, an observer looks at a central target spot and spots of light flash in different positions in the visual field. The observer's responses to the flashes of light builds up a map of the visual field.

Finally, with the Optokinetic Perimetry test, an observer is instructed to look, in turn, at a series of spots spaced round a central spot and asked if he can see the central spot while looking at each of the series of spots, thereby building up a map of the visual field.

Problems associated with the above tests stem from the fact that in each case the observer is required to give some sort of indication or response as to when they see the target in their visual field. The exact point of when the target is seen can be somewhat subjective and unclear and can therefore lead to significant inaccuracies.

An object of the present invention is to seek to overcome the problems associated with such known tests.

According to a first aspect of the present invention, there is provided a method for ocular testing, the method comprising the steps of:

1) providing a fixation target on a screen at a known target position;
2) detecting a direction of gaze of one or both eyes of an observer viewing the fixation target;
3) providing a new target on the screen at a further known target position;
4) detecting whether the direction of gaze moves to a direction that corresponds to direct viewing of the new target;
5) repositioning the new target if required until it is detected at step 4) that the direction of gaze corresponds to direct viewing of the new target, the new target then becoming the fixation target;
6) recording the target positions; and
7) repeating steps 3) to 6) a number of times to build up a visual field.

With such a method, the fixation target is a target onto which the observer is initially encouraged to fix his gaze. The new target is a visual field target provided somewhere on the screen in the visual field of a normal observer.

If the observer is aware of the visual field target while looking at the fixation target, then he is encouraged to fix his gaze on the visual field target which then becomes the fixation target at a revised known target position. This change in direction of gaze can be detected by an eye tracking means. The previous fixation target can then be repositioned so as to perform the function of the visual field or new target and the process is repeated to build up a visual field. With such a method no response from the observer is required to build up the visual field other than the automatic detection of the change in gaze direction by the eye tracking means.

Conveniently, the targets are moved under the control of a computer and data of the target positions and gaze directions is recorded to build up a full visual field of the observer. The screen may in this respect be provided at a known distance from the observer.

Preferably, the new target is only provided on the screen while the detected direction of gaze is on the current fixation target. This reduces the risk of false results from the testing.

With certain observers, a substantial part of the field on one side may missing such that as successive targets are presented, only those not in the missing part are seen. This could have an effect in gradually moving the fixation target further and further to one side of the display. Consequently, the useful area of the screen for presenting further targets will be diminished. To counter this the method may further comprise means for repositioning the fixation target on the display to allow a new target to be positioned on the screen.

The repositioning of the fixation target is preferably carried out with the fixation target in constant view of the observer. In this manner, the effect of the repositioning of the fixation target on the data on the visual field of the observer is readily reconciled.

According to a second aspect of the present invention there is provided a method of ocular testing for use with apparatus having a display means for displaying a target, an eye tracking means for tracking eye movement and a control means for controlling the display of the target on the screen; wherein the method comprises arranging the control means to choreograph display of the target at different positions on the screen depending on whether the eye tracking means detects that the observer is directly looking at the target.

The method preferably further comprises recording data from the control means and the eye tracking means.

According to a third aspect of the present invention, there is provided apparatus for visual field measurement; the apparatus comprising:
  a screen on which first and second targets can be simultaneously displayed at known target positions;
  eye tracking means for detecting a direction of gaze of one or both eyes of an observer viewing the targets;
  comparison means for comparing the direction of gaze detected by the eye tracking means with a direction of gaze that would be required to directly view the targets;
  control means for providing the targets at a number of different positions on the screen in response to the comparison means identifying whether the detected direction of gaze matches the direction of gaze that would be required to directly view the targets.

According to a fourth aspect of the present invention there is provided apparatus for visual field measurement; the apparatus comprising:
  a screen on which first and second targets can be simultaneously displayed at known target positions;
  eye tracking means for detecting a direction of gaze of one or both eyes of an observer viewing the targets;
  comparison means for comparing the direction of gaze detected by the eye tracking means with a direction of gaze that would be required to directly view the targets; and
  control means for providing the targets at a number of different positions on the screen in response to the comparison means identifying whether or not the detected direction of gaze matches the direction of gaze that would be required to directly view the targets.

In this regard and as discussed above, one of the first and second targets is initially a fixation target and the other a visual field target provided in the visual field of the observer.

The first and second targets will generally alternate as to their roles as fixation and visual field targets.

The control means preferably operates to reposition the target which has been identified as no longer matching the detected direction of gaze. Namely, once the eye tracking means has identified that the detected direction of gaze has left, say the first target acting previously as the fixation target, then the first target will be repositioned so that it functions as a visual field target.

Conveniently, the control means can operate to reposition the target not currently being directly viewed after a predetermined time interval. In this respect, this gives the observer an opportunity to establish whether such a target is in their visual field. If the observer is not aware of such a target then it is repositioned, for example closer to the fixation target, to try to establish the limits of the observer's visual field at that orientation.

Preferably, the control means operates to move the target not being directly viewed, in incremental steps. These steps should be small enough to accurately measure the visual field of the observer.

Whilst any suitable means for displaying the targets may be used, for example LCD, laser display or plasma screen technology, the apparatus may further comprise projection means for projecting the targets onto the screen and the components of the apparatus may be computer controlled. The computer may be programmed to alternately position the targets according to the responses of the eye tracking means to establish the visual field of the observer.

Preferably, data of target positions and gaze direction for the different target positions are recorded to form a visual field for the observer.

In preferred embodiments, the control means only provides a second target on the screen when the eye tracking means has confirmed that the observer's direction of gaze is directed at a first target on the screen. This reduces the risk of false positives and false negatives.

The apparatus may further comprise means for repositioning the fixation target on the display to allow a new target to be positioned on the screen. The repositioning of the fixation target is preferably carried out with the fixation target in constant view of the observer.

According to a fifth aspect of the present invention there is provided apparatus for ocular testing comprising a display means for displaying a target, an eye tracking means for tracking eye movement and a control means for controlling the display of the target on the screen;

wherein the control means choreographs the display of the target at different positions on the screen depending on whether the eye tracking means detects that the observer is directly looking at the target.

Examples of the present invention will now be described with reference to the accompanying drawings of which:

Figure 1:
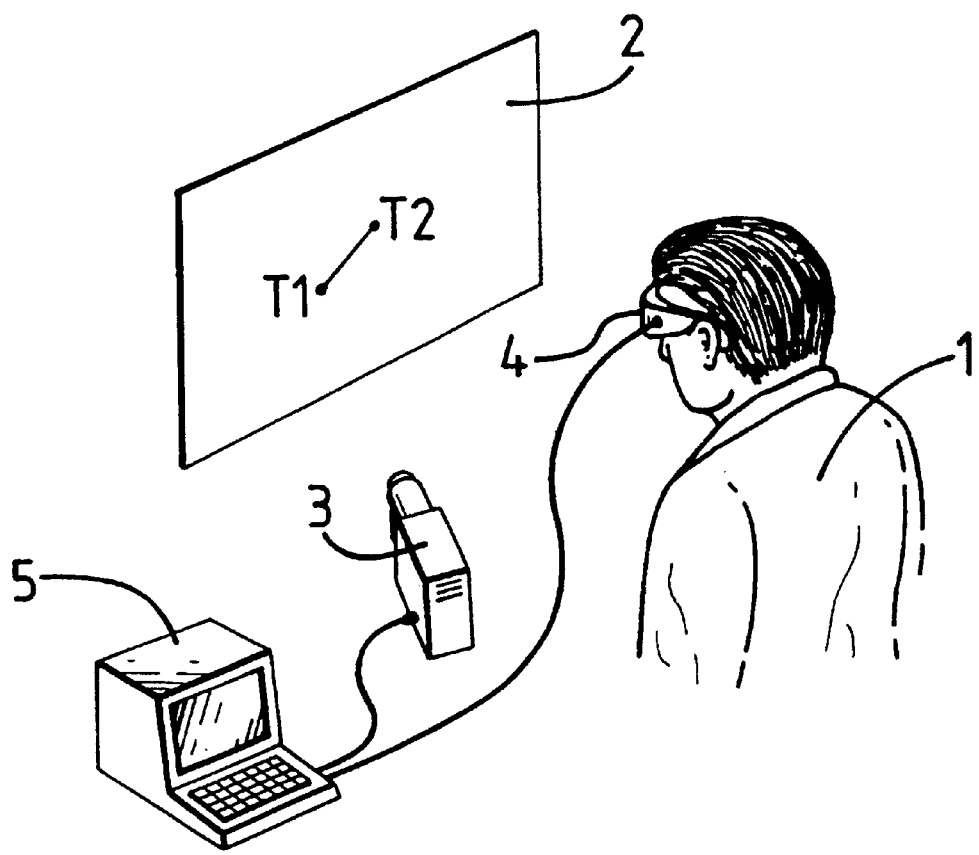
FIG. 1 shows diagrammatically apparatus for use in the present invention.

As shown in FIG. 1, an observer 1 is positioned to view a display 2 showing targets T1, T2 . . . In the present case the targets are projected onto the display 2 via a protector 3. Clearly however the display could take the form of any suitable means for displaying targets to an observer. For example, the display could involve the use of visual display units (VDU) arranged in a similar manner to that shown in FIG. 1 or alternatively small display units could be used, made up of for example, LCD (liquid crystal display) units, mounted within a pair of goggles or other headgear worn by the observer.

Suitable eye tracking means are provided within goggles 4. Data from the eye tracking means is fed back to a computer 5, which also controls the positioning and synchronisation of the display of the targets. Of course, any suitable means for tracking eye movement may be used, further details of such eye tracking means being discussed in my earlier patent GB2280505.

Figure 2:
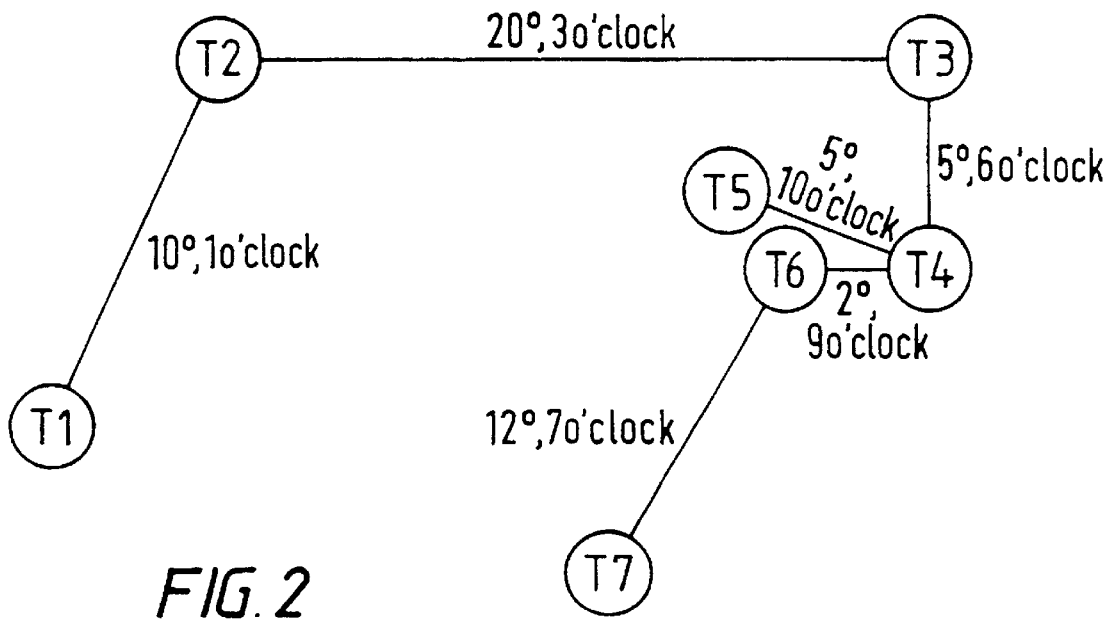
FIGS. 2 and 3 show schematically apparatus for use with the present invention.

FIG. 2 schematically shows a target T1 at the starting point of a visual field test. An observer is initially encouraged to look directly at this target. The eye tracker, of the sort commonly used in eye testing, monitors the gaze-direction of one or both of the observer's eyes. Once it is confirmed that the observer is looking directly at target T1, (e.g. using data from the eye tracker and the display), then target T1 becomes a fixation target. Target T2 is then provided on the screen as a visual field target and if the observer is aware of target T2, he is encouraged to direct his gaze to it, whereby it then becomes the new fixation target. At this point target T1 disappears and a new target, target T3 appears and the process continues for targets T4 to T7.

If a visual field target is not seen, it is either moved under computer control to where it is seen and the position recorded or other targets are displayed one at a time until one is seen and the process continues further. By varying the distance and 'clock' direction of the new visual field target in relation to the fixation target, which was the previous visual field target, a visual field can be built up. Hence, the observer simply follows targets appearing on the screen with his eye, the test not requiring him to say whether he sees the target or to produce any other response such as pressing a buzzer as in previous arrangements. Also with constant tracking of the eye, the computer will only display the next target while the eye was still directed at the existing target reducing the risk of false positives and false negatives.

Figure 3:
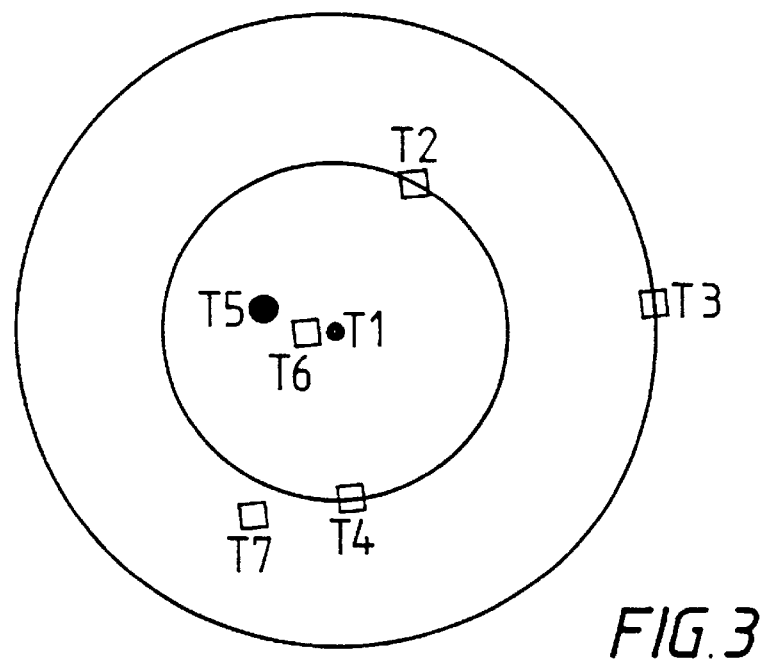

Referring to FIG. 3, this shows the visual field built up from the responses gained in relation to the test described above of FIG. 2. The circular dot shows target T5 as not being seen and the squares show targets T1–T4, T6 and T7 that were seen in the measurement test.

The apparatus may further comprise means for repositioning the display position of the fixation target to allow a new target to be positioned on the screen. In this respect, with certain observers, a substantial part of the field on one side may missing such that as successive targets are presented, only those not in the missing part are seen. This could have an effect in gradually moving the fixation target further and further to one side of the display. Consequently, the useful area of the screen for presenting further targets will be diminished. To counter this, with the fixation target in view to the observer, it is moved under the control of the computer to a position where there is sufficient space left on the display to present further targets and thus continue the test. Such a means for repositioning the target may for example be provided in the form of software of the computer.

It will be appreciated that the present invention may be applied to many different configurations, the detailed embodiments being straightforward for those skilled in the art to implement.

What is claimed is:

1. A method of ocular testing, the method comprising the steps of:

1) providing a fixation target on a screen at a known target position;

2) detecting a direction of gaze of one or both eyes of an observer to confirm he is viewing the fixation target;

3) providing a new target on the screen at a further known target position;

4) detecting whether the direction of gaze moves to a direction that corresponds to direct viewing of the new target;

5) repositioning the new target, if required, until it is detected at step 4) that the direction of gaze corresponds to direct viewing of the new target, the new target then becoming the fixation target;

6) recording the target positions: and 7) repeating steps 3) and 6) until a visual field is built.

2. A method according to claim 1, wherein the targets are moved under the control of a computer.

3. A method according to claim 1 or 2, wherein data of the target positions and gaze directions is stored to build up a visual field of the observer.

4. A method according to claim 1 or 2, wherein the new target is only provided on the screen while the detected direction of gaze is on the fixation target.

5. A method according to claim 1 or 2, further comprising the step of repositioning the fixation target whilst viewed by the observer to create additional space on the screen for displaying the new target.

6. A method according to claim 1 or 2 wherein a new target is not seen by the observer is repositioned after a predetermined time interval.

7. A method according to claim 1 or 2 wherein a new target not seen by the observer is moved in incremental steps.

8. A method according to claim 1 or 2, wherein the targets are projected onto the screen.

9. A method of ocular testing, the method comprising the steps of:

1) providing a fixation target on a screen at a known target position;

2) detecting a direction of gaze of one or both eyes of an observer to confirm he is viewing the fixation target;

3) providing a new target on the screen in addition to the fixation target, the new target being provided at a further known target position;

4) detecting whether the direction of gaze moves to a direction that corresponds to direct viewing of the new target;

5) repositioning the displayed new target, if required because it is not seen by the observer in their peripheral vision, until it is detected at step 4) that the direction of gaze corresponds to direct viewing of the new target, the new target then becoming the fixation target;

6) recording data of the target positions relative to eachother: and 7) repeating steps 3) and 6) a number of times to build up a visual field; wherein at step 2) the fixation target is moved if required, whilst being observed by the observer, to a position on the screen to thereby create additional space for displaying the new target.

10. Apparatus comprising a computer programmed to carry out the following steps:

1) provided a fixation target on a screen at a known target position;

2) detected a direction of gaze of one or both eyes of an observer to confirm he is viewing the fixation target;

3) provided a new target on the screen in addition to the fixation target, the new target being provided at a further known target position;

4) detected whether the direction of gaze moves to a direction that corresponds to direct viewing of the new target;

5) repositioned the new target being displayed, if required because it is not seen by the observer in their peripheral vision, until it is detected at step 4) that the direction of gaze corresponds to direct viewing of the new target, the new target then becoming the fixation target.

* * * * *